US012121673B2

(12) United States Patent
Spivey et al.

(10) Patent No.: US 12,121,673 B2
(45) Date of Patent: *Oct. 22, 2024

(54) RIGID AND FLEXIBLE LAPAROSCOPIC MULTIPLE COMPONENT MATERIAL DISPENSING DEVICES AND METHODS

(71) Applicant: ETHICON LLC, San Lorenzo (TR)

(72) Inventors: James T. Spivey, Whitehouse Station, NJ (US); Michael J. Trezza, Long Valley, NJ (US); John Goodman, Ann Arbor, MI (US); Michael J. Vendely, Lebanon, OH (US); Michael Setser, Burlington, OH (US)

(73) Assignee: Ethicon, Inc., Raritan, NJ (US)

( * ) Notice: Subject to any disclaimer, the term of this patent is extended or adjusted under 35 U.S.C. 154(b) by 1038 days.

This patent is subject to a terminal disclaimer.

(21) Appl. No.: 16/908,387

(22) Filed: Jun. 22, 2020

(65) Prior Publication Data
US 2020/0316338 A1    Oct. 8, 2020

Related U.S. Application Data

(63) Continuation of application No. 15/392,970, filed on Dec. 28, 2016, now Pat. No. 10,737,058.

(51) Int. Cl.
A61M 25/00   (2006.01)
A61B 17/00   (2006.01)
(Continued)

(52) U.S. Cl.
CPC ... A61M 25/0026 (2013.01); A61B 17/00234 (2013.01); A61B 17/00491 (2013.01);
(Continued)

(58) Field of Classification Search
CPC .......... A61M 25/0026; A61M 25/0028; A61M 25/0029; A61M 25/003; A61M 25/0032;
(Continued)

(56) References Cited

U.S. PATENT DOCUMENTS 4,046,479 A    9/1977 Paley
4,932,942 A *  6/1990 Maslanka ................ A61B 1/12
                                                                 604/44
(Continued)

FOREIGN PATENT DOCUMENTS

CN    102740779 A    10/2012
CN    104159625 A    11/2014
(Continued)

OTHER PUBLICATIONS

Office Action for related European Patent Application No. 17 817 514.7-1122, dated Jul. 4, 2023, 9 pages.
(Continued)

Primary Examiner — Kevin C Sirmons
Assistant Examiner — Alexandra Lalonde

(57) ABSTRACT

A dispensing device to deliver a multiple component material to a location in vivo. The device includes a manifold having proximal and distal ends and multiple separate lumens within it, connectable on its proximal end to multiple syringes for containing the multiple component material, a distal tip assembly comprising a tip connector having separate side-by-side lumens within the tip connector and optionally a dispensing tip, and multiple flexible side-by-side cannulae. Each cannulae has a proximal end and a distal end, the proximal ends of the cannulae are connected to a separate lumen at the distal end of the manifold, and the distal ends of the cannulae are connected to one of the side-by-side lumens of the tip connector, establishing a fluid communication between the manifold and the distal tip assembly, wherein the side-by-side cannulae are optionally partially connected along their length and are split at their proximal and distal ends.

47 Claims, 13 Drawing Sheets

(51) Int. Cl.
  *A61M 5/315* (2006.01)
  *A61M 37/00* (2006.01)
  *A61M 39/10* (2006.01)

(52) U.S. Cl.
  CPC ........ *A61M 5/31596* (2013.01); *A61M 37/00* (2013.01); *A61M 39/10* (2013.01); *A61B 2017/00292* (2013.01); *A61B 2017/00495* (2013.01); *A61B 2017/00526* (2013.01); *A61M 2025/0037* (2013.01); *A61M 2039/1033* (2013.01); *A61M 2039/1077* (2013.01)

(58) Field of Classification Search
  CPC ...... A61M 25/0041; A61M 2025/0034; A61M 2025/0035; A61M 2025/0036; A61M 2025/0037; A61M 5/00; A61M 5/19; A61M 5/3129; A61M 39/10; A61M 2039/1033; A61M 2039/1077; A61M 37/00; A61M 25/0014; A61M 25/0097; A61M 25/0067; A61M 25/0068; A61M 25/0069; A61M 25/0071; A61M 5/31596; A61M 5/1407; A61M 5/1408; A61M 5/2066; A61M 5/2448; A61M 5/344; A61M 5/345; A61M 39/105; A61M 39/12; A61M 39/08; A61M 39/00; A61M 2039/1083; A61M 2039/1088; A61M 2039/082; A61M 2039/0009; A61M 2039/0027; A61M 2005/31598; A61B 17/00234; A61B 17/00491; A61B 2017/00292; A61B 2017/00495; A61B 2017/00522
  See application file for complete search history.

(56) References Cited

U.S. PATENT DOCUMENTS

| | | | |
|---|---|---|---|
| 4,979,942 A | 12/1990 | Wolf et al. | |
| D358,471 S | 5/1995 | Cope et al. | |
| 5,562,689 A | 10/1996 | Green et al. | |
| D376,649 S | 12/1996 | Kim | |
| 5,814,022 A | 9/1998 | Antanavich et al. | |
| D442,553 S | 5/2001 | Urban et al. | |
| D456,509 S | 4/2002 | Schultz | |
| 6,494,896 B1 | 12/2002 | D'Alessio et al. | |
| 6,884,232 B1 | 4/2005 | Hagmann et al. | |
| 6,921,381 B2 | 7/2005 | Spero et al. | |
| D523,557 S | 6/2006 | Jones et al. | |
| 7,077,339 B2 | 7/2006 | Leach | |
| D534,650 S | 1/2007 | Inman et al. | |
| 8,088,099 B2 | 1/2012 | Mcintosh et al. | |
| D682,422 S | 5/2013 | Anderson et al. | |
| 8,460,235 B2 | 6/2013 | Keller | |
| 8,684,282 B2 | 4/2014 | Steffen | |
| 8,974,436 B2 | 3/2015 | Sherman et al. | |
| 9,022,975 B2 | 5/2015 | Goodman et al. | |
| 9,125,633 B2 | 9/2015 | Roush et al. | |
| 2002/0138038 A1 | 9/2002 | Ljungquist | |
| 2003/0065246 A1 | 4/2003 | Inman et al. | |
| 2006/0253082 A1 | 11/2006 | Mcintosh et al. | |
| 2007/0157985 A1 | 7/2007 | Caro et al. | |
| 2007/0288048 A1 | 12/2007 | Ortiz et al. | |
| 2008/0060970 A1 | 3/2008 | Wheeler et al. | |
| 2009/0108091 A1 | 4/2009 | Steffen | |
| 2009/0143794 A1 | 6/2009 | Conlon et al. | |
| 2010/0121268 A1 | 5/2010 | Keller | |
| 2011/0092899 A1 | 4/2011 | Ohri et al. | |
| 2014/0014213 A1* | 1/2014 | Hull | A61B 17/00491 137/883 |
| 2015/0216516 A1 | 8/2015 | Steffen | |
| 2015/0327846 A1* | 11/2015 | Hull | B05B 1/3436 606/214 |
| 2017/0100115 A1* | 4/2017 | Mathys | A61B 17/00491 |

FOREIGN PATENT DOCUMENTS

| | | |
|---|---|---|
| DE | 4223356 A1 | 1/1994 |
| EA | 005619848-0001 | 11/2018 |
| EA | 005619848-0002 | 11/2018 |
| EP | 3020343 A1 | 5/2016 |
| GB | 6042339 | 8/2018 |
| GB | 6042340 | 8/2018 |
| JP | 2011-083603 A | 4/2011 |
| JP | 2011-167341 A | 9/2011 |
| JP | 2015-142613 A | 8/2015 |
| WO | 0006216 A1 | 2/2000 |
| WO | 03039375 A2 | 5/2003 |
| WO | 2009132331 A1 | 10/2009 |
| WO | 2014207920 A1 | 12/2014 |
| WO | 2015/176905 A1 | 11/2015 |
| WO | 2015/004709 A1 | 2/2017 |

OTHER PUBLICATIONS

Medical product outsourcing Magazine. Link: https://www.mpo-mag.com/contents/view_breaking-news/2017-06-20/fda-clears-bds-customizable-micro-laparoscopic-instruments. Jun. 20, 2017. FDA Clears BD's Customizable Micro-Laparoscopic Instruments. (Year: 2017).

International Search Report & Written Opinion for related PCT Application No. PCT/US2017/063619, dated Mar. 29, 2018.

Translation of Search Report for related Chinese Patent Application No. 201780081431.7, received Jun. 8, 2023, 3 pages.

Office Action for related Australian Patent Application No. 2017386122, dated Jul. 20, 2022, 3 pages.

Translation of Notification of Reasons for Refusal for related Japanese Patent Application No. 2019-535227, Sep. 21, 2021, 10 pages.

Office Action for related Brazilian Patent Application No. BR112019013263-5, dated Feb. 24, 2022, 8 pages, with Google Translation.

* cited by examiner

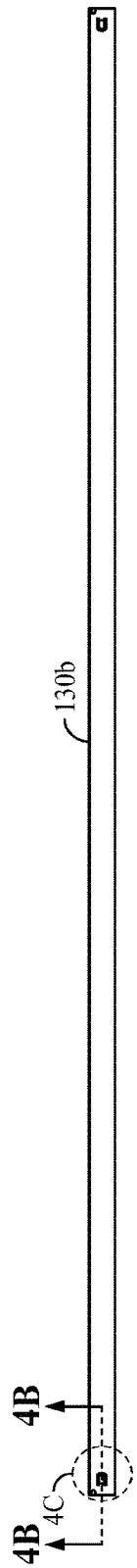
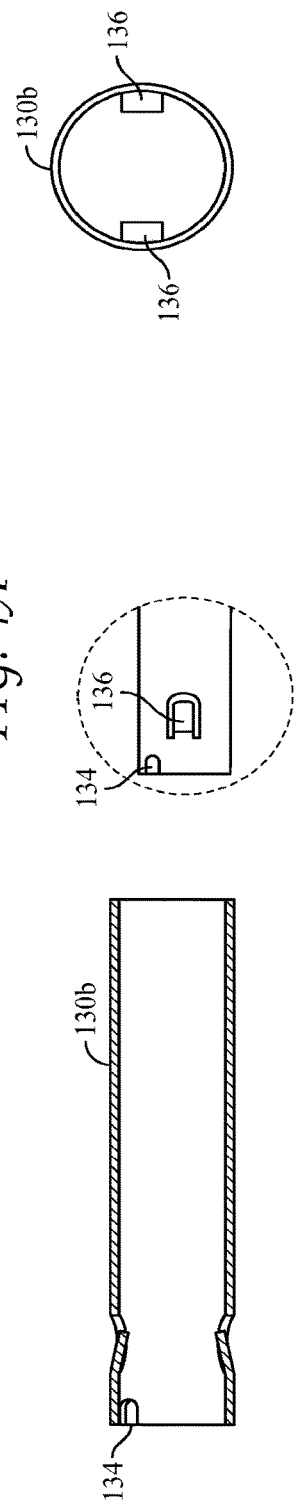
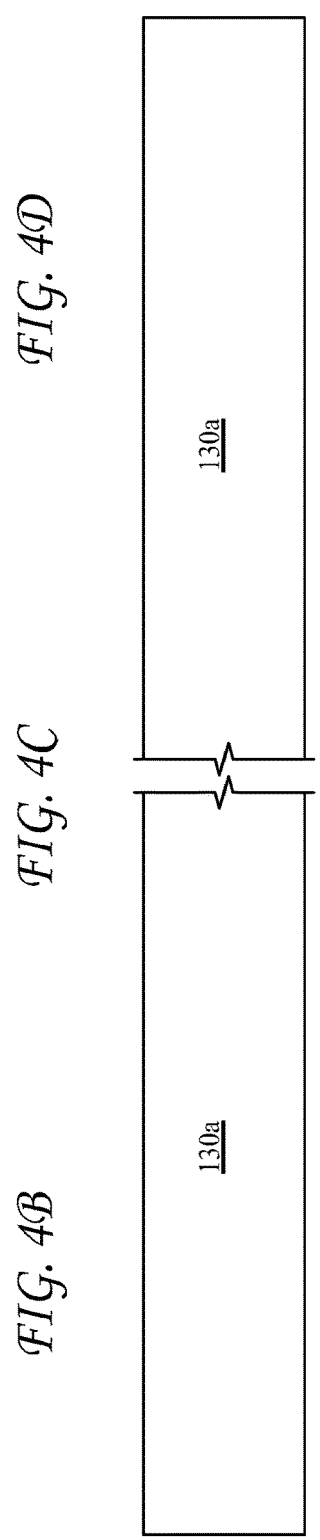
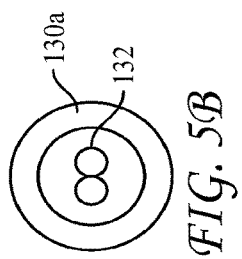
FIG. 4A
FIG. 4B
FIG. 4C
FIG. 4D
FIG. 5A
FIG. 5B

RIGID AND FLEXIBLE LAPAROSCOPIC MULTIPLE COMPONENT MATERIAL DISPENSING DEVICES AND METHODS

CROSS REFERENCE TO RELATED APPLICATIONS

This application is a continuation of U.S. application Ser. No. 15/392,970, filed Dec. 28, 2016, entitled "Rigid and Flexible Laparoscopic Multiple Component Material Dispensing Devices and Methods," now U.S. Pat. No. 10,737,058, the entirety of which is incorporated herein by reference.

FIELD

This invention relates to a dispensing device for multiple component materials used in medical or surgical procedures. Environment In recent years, minimally invasive surgical techniques have emerged as an alternative to conventional surgical techniques to perform a plurality of surgical procedures. Minimally invasive procedures differ from conventional surgical procedures in that a plurality of devices may be introduced into the body through a small incision. As a result, trauma to the body is greatly reduced, thereby decreasing the recovery time of the patient.

One example of a common minimally invasive surgery involves laparoscopic surgical procedures. Laparoscopic procedures may be used to treat hernias, colon dysfunctions, gastroesophageal reflux disease, gallbladder disorders, etc. Typically, the patient undergoing the procedures will return home hours after undergoing surgery.

One challenge presented when performing minimally invasive surgical procedures relates to closing an incision made within the patient's body by a cutting laparoscopic instrument. As opposed to conventional surgical procedures, the surgeon's access to the site of the incision is greatly reduced during minimally invasive procedures.

Recently, the use of tissue sealants and other biological adhesive materials has emerged as an alternate technique of closing incisions. Such tissue sealants may include fibrin, which is comprised of thrombin and a fibrinogen material, although other multiple component materials are available. Typically, the individual components of the adhesive material are stored in isolated reservoirs. When mixed, these components may coagulate very quickly, yielding an adhesive gel within a short period of time, perhaps 10 or 20 seconds. When applied to the exterior of the body, or when considerable access to the application site is possible, the rapid coagulative properties of the tissue sealant are advantageous. However, such fast-acting properties of conventional tissue sealants and adhesive have presented potential problems of fouling or clogging during the application of tissue sealants through laparoscopic devices, which typically results in the destruction of the device.

Additionally, it is difficult to manufacture flexible accessories for delivering a two component material to a location in vivo. The components of the material are stored separately in and expressed out of a dual syringe, which requires a minimum distance between the exit orifices of the dual syringe. To be functional, the flexible cannula must be significantly smaller than the minimum distance between the exit orifices of the dual syringe, which results in two physically separated fluid paths coming together to fit into the cannula.

Multilumen tubing is difficult to extrude and cut while providing patency of each lumen, repeatable shapes, and clean surfaces for bonding. Current devices and methods use very challenging overmolding processes with bent core pins, which results in high scrap rates, or use additional components such as bent hypotubes, which add cost and complexity to the assembly of the device.

Thus, there is a need for a device capable of effectively delivering a multiple component tissue sealant to a location in vivo from a remote location, which is easily and reproducibly manufactured.

SUMMARY

Presented herein is a dispensing device to deliver a multiple component material to a location in vivo, the device comprising a manifold having proximal and distal ends and multiple separate lumens within it, connectable on its proximal end to multiple syringes for containing the multiple component material, a distal tip assembly comprising a tip connector having separate side-by-side lumens within the tip connector and optionally a dispensing tip, and multiple flexible side-by-side cannulae, each having a proximal end and a distal end, the proximal ends of the cannulae each connected to a separate lumen at the distal end of the manifold, and the distal ends of the cannulae each connected to one of the side-by-side lumens of the tip connector, establishing a fluid communication between the manifold and the distal tip assembly, wherein said side-by-side cannulae are optionally partially connected along their length and are split at their proximal and distal ends.

In one form, the tip connector is provided with an external thread for connecting a threaded dispensing tip and a barbed proximal end.

In one form, the distal ends of the cannulae are retained within the side-by-side lumens of the tip connector with an adhesive or by overmolding the cannulae in the lumens.

In another form, the dispensing device further comprises a housing enclosing at least a portion of the cannulae and the manifold.

In yet another form, the tip connector comprises a distal end having two apertures, each in fluid connection with one of the side-by-side lumens therein, and can further include at least one flat surface on an outer surface thereof, or even multiple flat surfaces on an outer surface thereof.

In one form, the dispensing device further comprises a rigid overtube through which the side-by-side cannulae extend, the rigid overtube extending between the distal tip assembly and a housing enclosing at least a portion of the manifold.

In another form, a barbed proximal end of the tip connector is disposed in a distal end of the rigid overtube, and the rigid overtube comprises at least one tab biased inward to retain the tip connector.

In yet another form, the barbed proximal end of the tip connector is disposed in a distal end of the rigid overtube, and the rigid overtube comprises at least one slot in the distal end of the rigid overtube to align with a keying feature of the tip connector to resist rotation of the tip connector in the rigid overtube.

In another form, the dispensing device comprises a flexible overtube and a grommet through which the side-by-side cannulae extend, the grommet being disposed in a distal end of a housing enclosing at least a portion of the manifold, and the flexible overtube extending between the tip connector and into the grommet.

Advantageously, the grommet comprises a barbed distal end over which the flexible overtube is disposed and the tip connector comprises a barbed proximal end over which the flexible overtube is disposed.

Conveniently, the flexible side-by-side cannulae are partially connected along their length.

In one form, the manifold of the dispensing device is a U- or H-shaped connector, hereinafter described as an H-connector, having two separate lumens extending therethrough, such as wherein the distal ends of the two separate lumens in the H-connector each comprise a first region and a second region, the first region being distal with respect to the second region, the first region having a diameter greater than the second region. In this form, the first region has a greater taper than the second region.

Conveniently, the proximal ends of the cannulae are retained within the second regions of the two separate lumens with an adhesive or by overmolding the cannulae in the lumens.

In another form, the proximal ends of the manifold comprise Luer-taper connections for the syringes. Optionally, the manifold is slidably disposed within the housing and the Luer-taper connections provide for an angular displacement relative to a centrally aligned position Advantageously, the dispensing device further comprises a brace disposed at a proximal end of the housing to secure the manifold therein, extending proximally from the housing to engage with a frame for the syringes, to align the syringes with the manifold.

Additionally presented is a method for delivering a multiple component material to a location in vivo, comprising supplying separate components of the multiple component material in separate syringes, compressing plungers of the separate syringes to deliver the multiple components to a manifold within a housing, the manifold having proximal and distal ends and multiple separate lumens within it, connected on its proximal end to the syringes and on its distal end to multiple flexible side-by-side cannulae, each having a proximal end and a distal end, the proximal ends of the cannulae each connected to a separate lumen at the distal end of the manifold, the distal ends of the cannulae connected to a distal tip assembly comprising a tip connector having separate side-by-side lumens within the tip connector and optionally a dispensing tip, each lumen connected to one of the flexible side-by-side cannulae, wherein said side-by-side cannulae are optionally partially connected along their length and are split at their proximal and distal ends, and passing the multiple components into the tip connector, optionally through the dispensing tip and then to the in vivo location.

In one form, the multiple flexible side-by-side cannulae have a rigid overtube extending between the manifold housing and the tip connector.

In another form, the multiple flexible side-by-side cannulae have a flexible overtube extending between the manifold housing and the tip connector.

Advantageously, the separate components do not contact one another until entering or exiting the dispensing tip.

BRIEF DESCRIPTION OF THE DRAWINGS

The forms disclosed herein are illustrated by way of example, and not by way of limitation, in the figures of the accompanying drawings and in which like reference numerals refer to similar elements and in which:

FIGS. 4A to 4D are views of the rigid overtube useful with the delivery device;

FIGS. 5A and 5B are views of the flexible overtube useful with the delivery device;

DETAILED DESCRIPTION

Figure 1A:
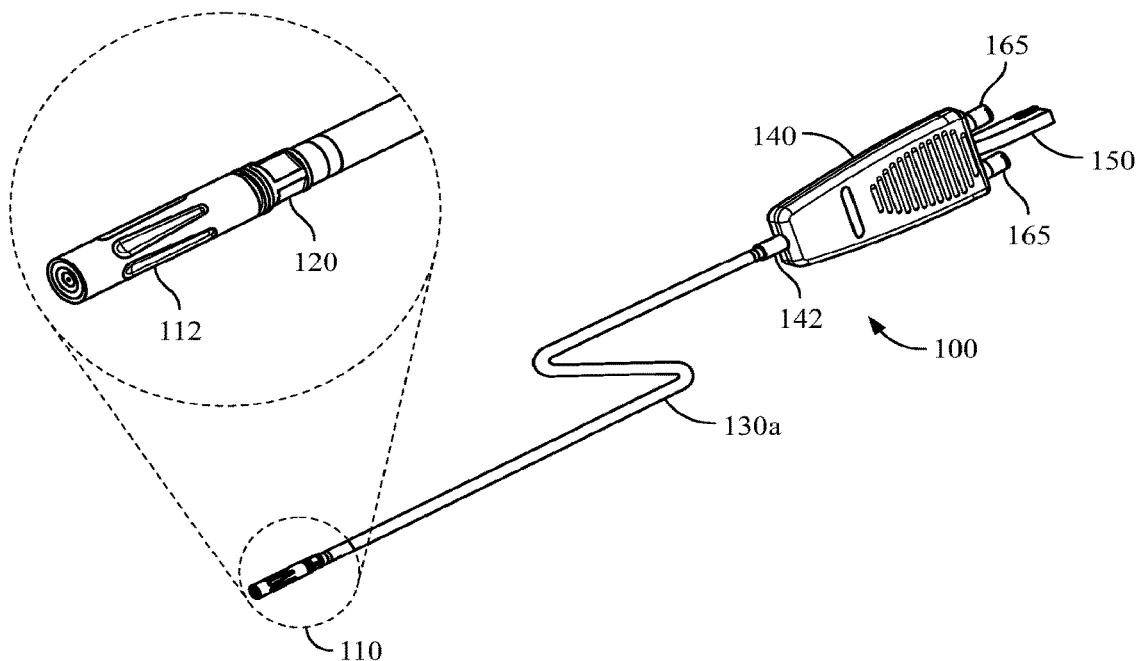
FIG. 1A is an illustration of a delivery device having a flexible overtube.

Described herein is a medical device and process for maintaining reactive components of a multiple component material separate for as long as possible, especially during delivery to a location at which they are to be mixed and reacted.

Each of the following terms written in singular grammatical form: "a," "an," and "the," as used herein, may also refer to, and encompass, a plurality of the stated entity or object, unless otherwise specifically defined or stated herein, or, unless the context clearly dictates otherwise. For example, the phrases "a device," "an assembly," "a mechanism," "a component," and "an element," as used herein, may also refer to, and encompass, a plurality of devices, a plurality of assemblies, a plurality of mechanisms, a plurality of components, and a plurality of elements, respectively.

Each of the following terms: "includes," "including," "has," "having," "comprises," and "comprising," and, their linguistic or grammatical variants, derivatives, and/or conjugates, as used herein, means "including, but not limited to."

It is to be understood that the various forms disclosed herein are not limited in their application to the details of the order or sequence, and number, of steps or procedures, and sub-steps or sub-procedures, of operation or implementation of forms of the method or to the details of type, composition, construction, arrangement, order and number of the system, system sub-units, devices, assemblies, sub-assemblies, mechanisms, structures, components, elements, and configurations, and, peripheral equipment, utilities, accessories, and materials of forms of the system, set forth in the following illustrative description, accompanying drawings, and examples, unless otherwise specifically stated herein. The apparatus, systems and methods disclosed herein can be practiced or implemented according to various other alternative forms and in various other alternative ways.

It is also to be understood that all technical and scientific words, terms, and/or phrases, used herein throughout the present disclosure have either the identical or similar meaning as commonly understood by one of ordinary skill in the art, unless otherwise specifically defined or stated herein. Phraseology, terminology, and, notation, employed herein throughout the present disclosure are for the purpose of description and should not be regarded as limiting.

Presented herein is a dispensing device to deliver a multiple component material to a location in vivo, the device comprising a manifold having proximal and distal ends and multiple separate lumens within it, connectable on its proximal end to multiple syringes for containing the multiple component material, a distal tip assembly comprising a tip connector having separate side-by-side lumens within the tip connector and optionally a dispensing tip, and multiple flexible side-by-side cannulae, each having a proximal end and a distal end, the proximal ends of the cannulae each connected to a separate lumen at the distal end of the manifold, and the distal ends of the cannulae each connected to one of the side-by-side lumens of the tip connector, establishing a fluid communication between the manifold and the distal tip assembly, wherein said side-by-side cannulae are optionally partially connected along their length and are split at their proximal and distal ends.

Aspects of the disclosed device provide a robust and simple design for delivering a multiple component material to a location, especially a location in vivo. In one form, the device incorporates side-by-side cannulae which are connected at their proximal ends to a manifold for delivering the multiple component material, and at their distal ends to the side-by-side lumens of a tip connector, such that fluid communication is established between the manifold and the tip connector through the side-by-side cannulae. Optionally, the side-by-side cannulae can be in the form of a "paratube", which is two extruded cannulae pressed together along their long axes, side-by-side, before the cooling quench of the extrusion process. The resulting paratube provides two separate, flexible, side-by-side cannulae connected, or heat sealed, together but still separable, completely or along only a desired length of the paratube. In a fibrin sealant application accessory, the paratube is split along a portion of its length, and at the split, individual cannula for conveying each component of a fibrin sealant are disposed and adhered to various Luer-type adapters via several different routes.

For example, the paratube may extend between a proximal manifold and a distal tip assembly via a grommet and a housing. In such case, the paratube may extend between the grommet and the distal tip assembly through a flexible overtube. As another example, the paratube may extend between the proximal manifold and the distal tip assembly via a rigid overtube disposed at least partially in the housing.

Further, whether the dispensing device is flexible or rigid, the housing may include a brace to engage and align a dual syringe containing the multiple component material or the housing may be configured to accept a brace to engage and align a dual syringe and to secure the manifold in the housing.

Figure 1B:
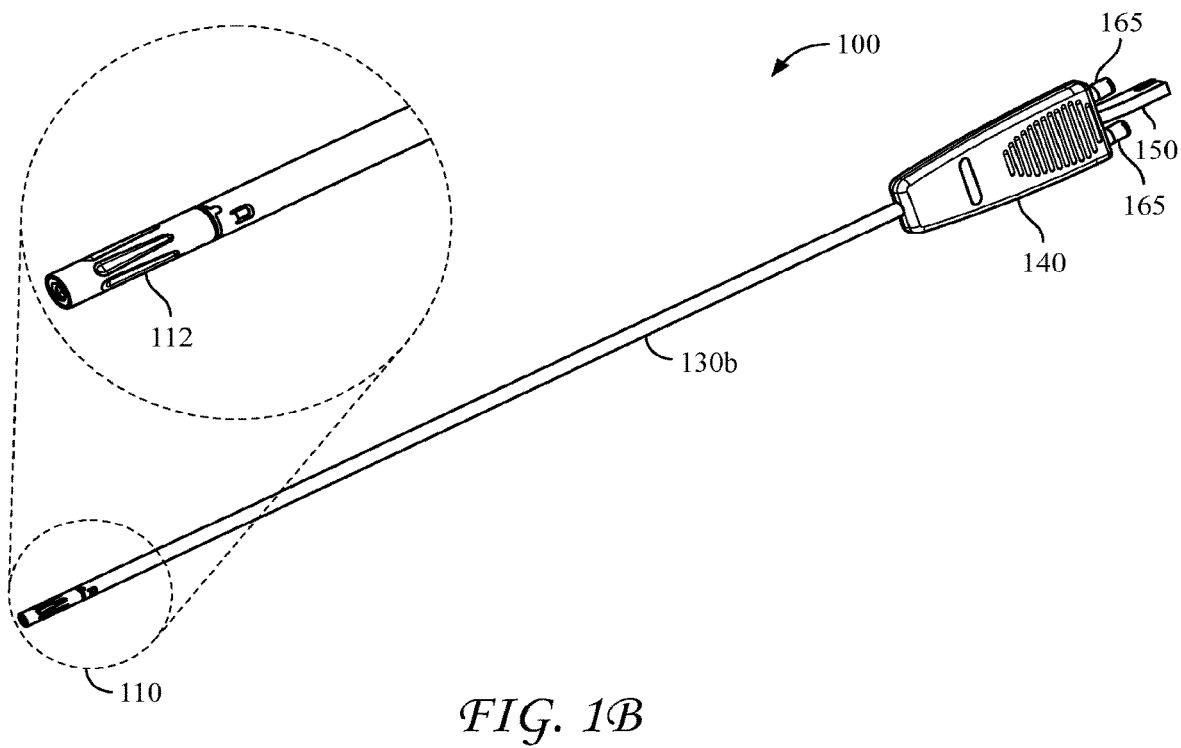
FIG. 1B is an illustration of the device having a rigid overtube.
Figure 1C:
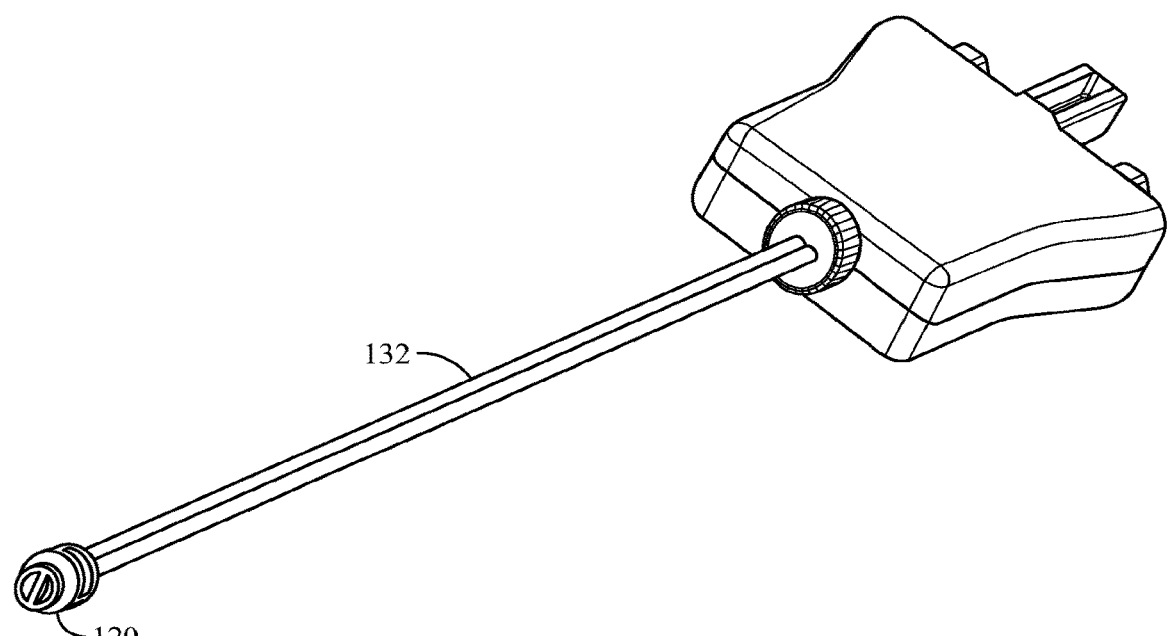
FIG. 1C is a distal view of either device of FIG. 1A or 1B without the overtube.
Figure 1D:
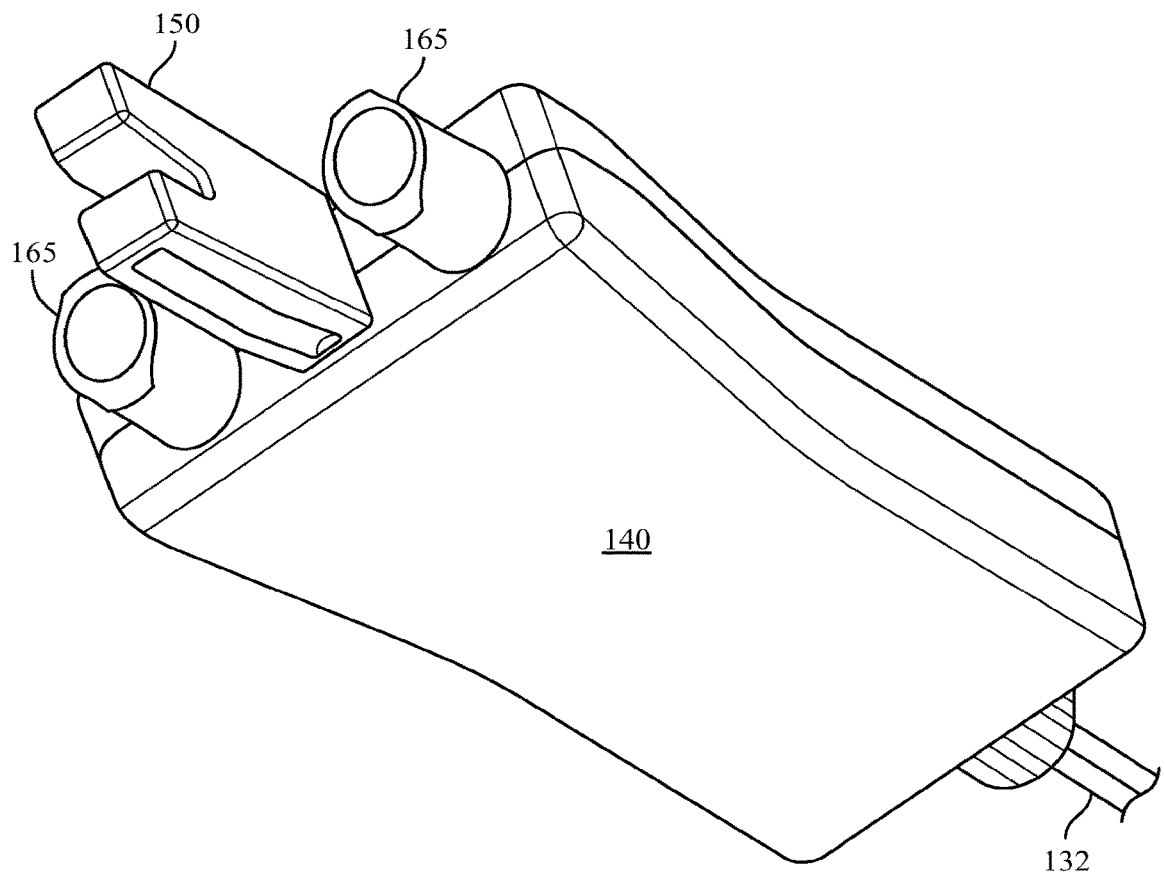
FIG. 1D is a view of the proximal end of the device housing.

FIGS. 1A and 1B illustrate overall views of the presently disclosed delivery device 100, except that FIG. 1A shows the flexible version of the device and FIG. 1B shows the rigid version of the device. Each version has a distal tip assembly 110 which comprises at least a tip connector 120 (not shown in FIG. 1B) and optionally a dispensing tip 112. The dispensing tips are for the most part conventional and can be used as either spray-type or drip-type tips. Also, each version has a housing 140 which encloses a manifold (not shown) from which Luer-type connections 165 extend from the proximal side of the housing, for connection to multiple syringes containing the multiple component material. The flexible version of the delivery device has a flexible overtube 130a which fits into a supporting grommet 142 in housing 140, while the rigid version has a rigid overtube 130b which fits directly into housing 140, both overtubes encasing the side-by-side cannulae or a paratube 132 (FIG. 1C), which side-by-side cannulae can be cut to different lengths overall to accommodate the different lengths of the flexible and rigid versions of the delivery device. It should be noted that the device can be structured and arranged without an overtube, if desired. FIG. 1D shows the proximal end of housing 140 with Luer-type connections 165 extending through the housing, and a brace 150, structured and arranged to connect to a frame for containing the multiple syringes. The brace provides for both easy alignment of the syringe tips and resistance to rotational torque on the housing, to provide a load path for any torque moment between the syringes and the housing so as to not damage the Luer connections.

FIGS. 2A through 2G illustrate the tip connector 120 which has a conical, barbed proximal end 122 and in this form a threaded distal end 124, to accommodate conventional dispensing tips 112 having matching internal threads, which can be used in a spray-type or drip-type mode, depending on the extent of pressure exerted on the syringes containing the multiple component material. Of course, the connection can be varied to any suitable and sturdy connection, such as for example a snap-type connection, wherein tip connector 120 has an annular bead around the outer circumference on the distal end and the dispensing tip 112 has a matching undercut on its inner circumference. The barbed proximal end 122 of the tip connector 120 is structured and arranged to fit securely within either the flexible overtube 130a or the rigid overtube 130b, as will be discussed below. Tip connector 120 is configured to have at least one flat surface 126 on its exterior surface, or even multiple flat surfaces 126, which make manipulation of the tip connector 120 with a medical provider's gloved hands much easier. For example, if the dispensing tip 112 becomes clogged by premature mixing of the thrombin and fibrinogen materials, the dispensing tip can be more easily removed and replaced by the medical worker gripping the flat surfaces 126 of tip connector 120, as compared to a connector having an annular circumference on the exterior surface. This is especially true when the tip connector 120 has a threaded distal end 124 and removal and replacement of the dispensing tip 112 requires holding the tip connector 120 steady while the clogged dispensing tip 112 is unscrewed.

Tip connector 120 is also provided with two separate, side-by-side lumens 121a and 121b which extend through the connector and match the orientation of the side-by-side cannulae 132 of in this case a paratube on the proximal end (FIG. 2E) of the tip connector 120. The diameters of lumens 121a and 121b are slightly larger than those of the cannulae, such that the side-by-side cannulae can be split at the distal end and separately inserted into lumens 121a and 121b. Advantageously, an adhesive is deposited in lumens 121a and 121b before or after insertion of the separated cannulae to fix them into place within the tip connector 120. Alternatively, the tip connector can be overmolded onto the tubing (either split and slightly separated, or not), or the tubing could be cut to slightly different lengths to minimize the chance of premature contact of the multiple components of the multiple component material in the instance that the over-molding is not completely sealed to the tubing.

The distal end of tip connector 120 can be provided with "D" shaped exit ports 125a and 125b (FIG. 2F), which are larger in size than lumens 121a and 121b, and thus easier to unclog, if necessary.

Figure 2A:
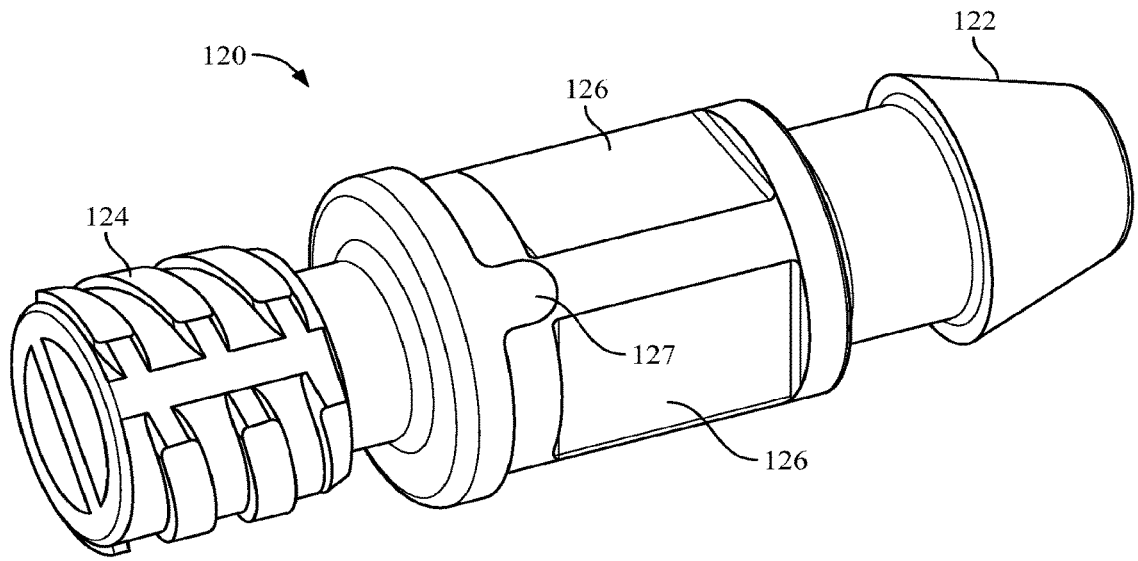
FIGS. 2A to 2G are views of the tip connector of the delivery device.
Figure 2B:
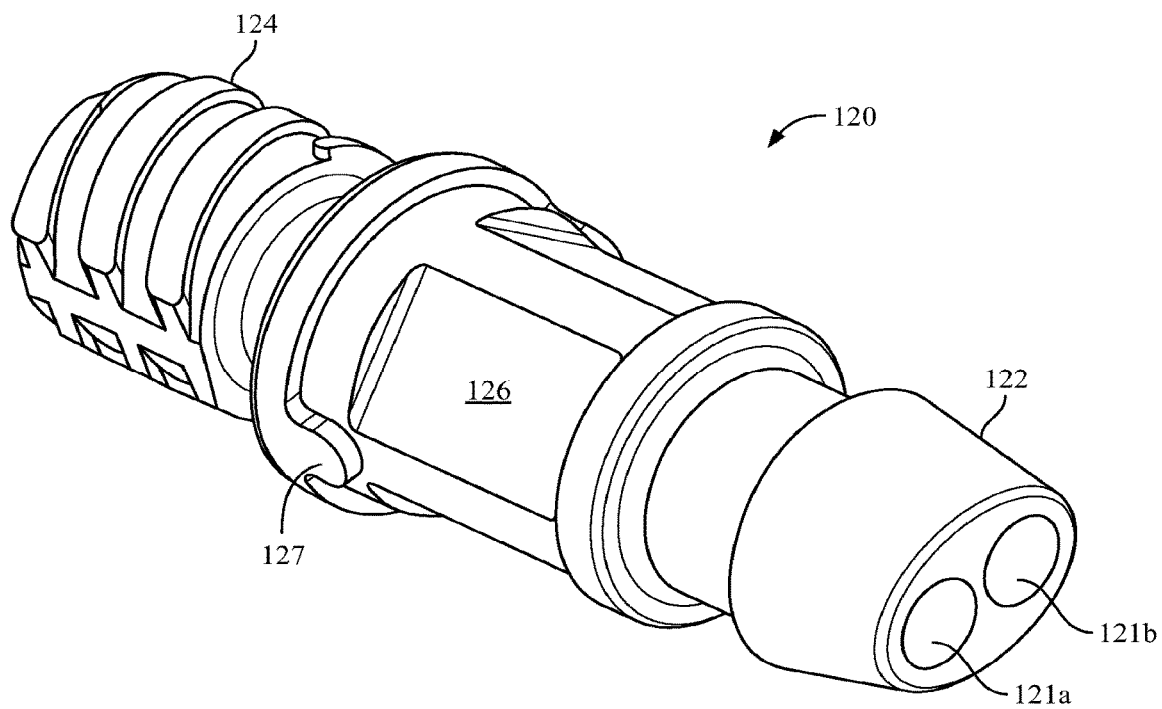
Figures 2C, 2D:
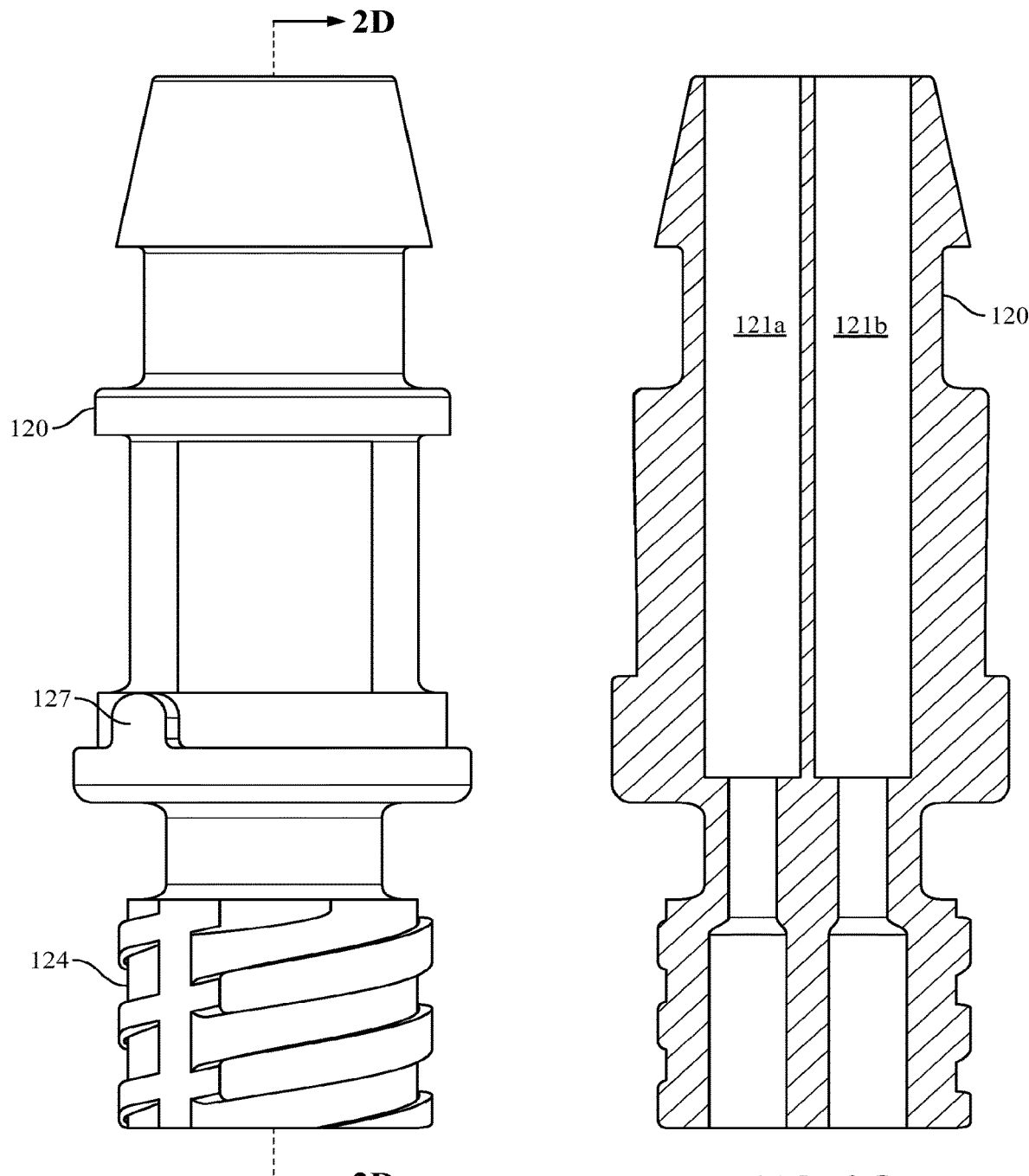
Figure 2E:
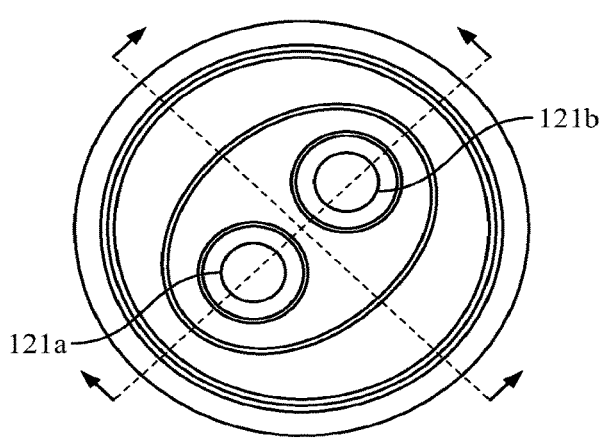
Figure 2F:
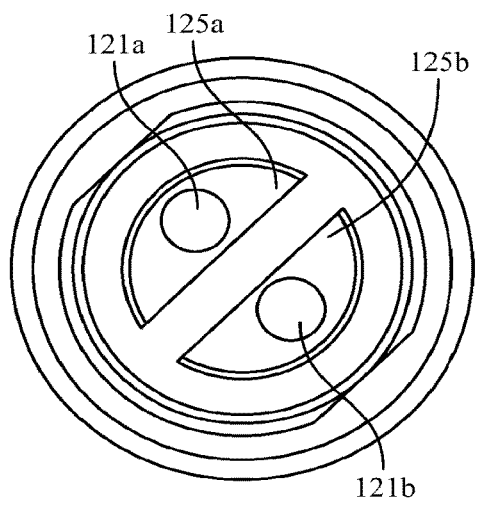
Figure 2G:
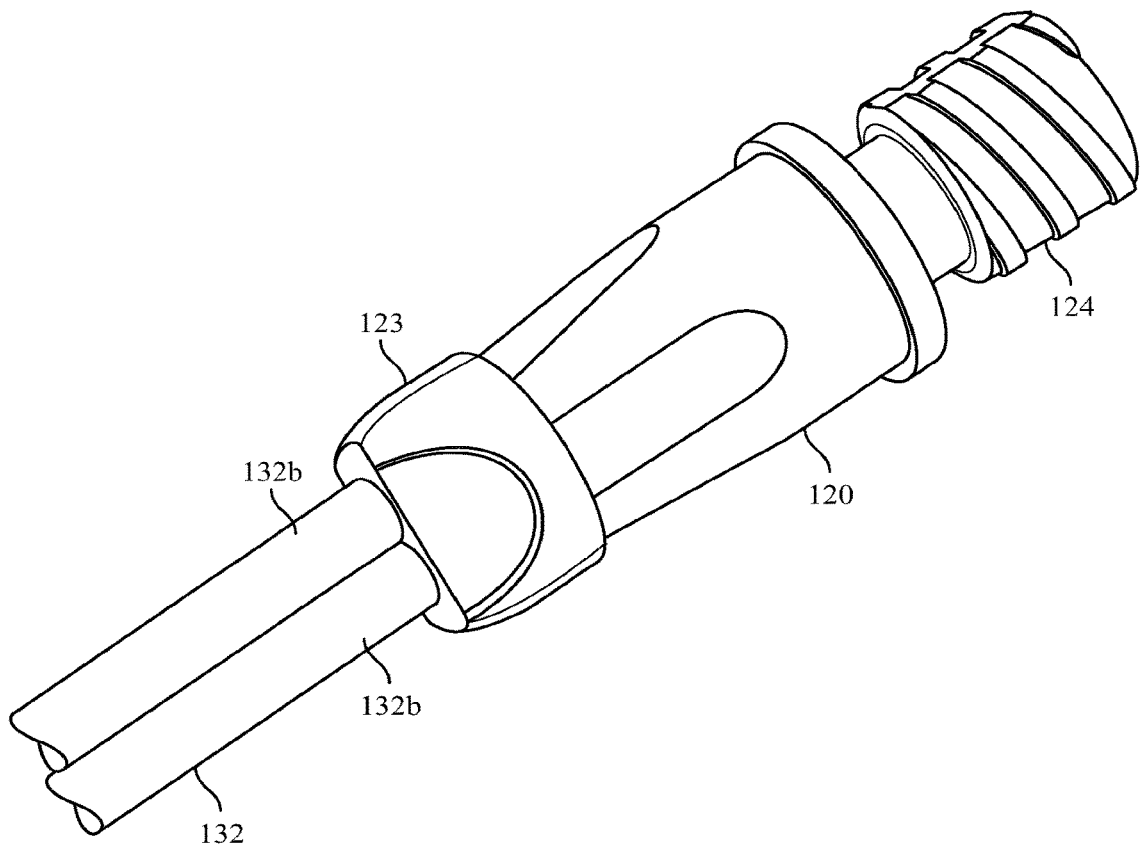

Tip connector 120 is additionally provided with a keying feature 127, which helps to resist rotation of the tip connector 120 when it is used with a rigid overtube. The particulars of this structure will be described in more detail below. FIG. 2G shows an alternative tip connector 120 design, wherein the barbed proximal end 123 is relatively flat rather than conical. In this view the insertion of separated distal cannulae 132b is evident.

Figure 3A:
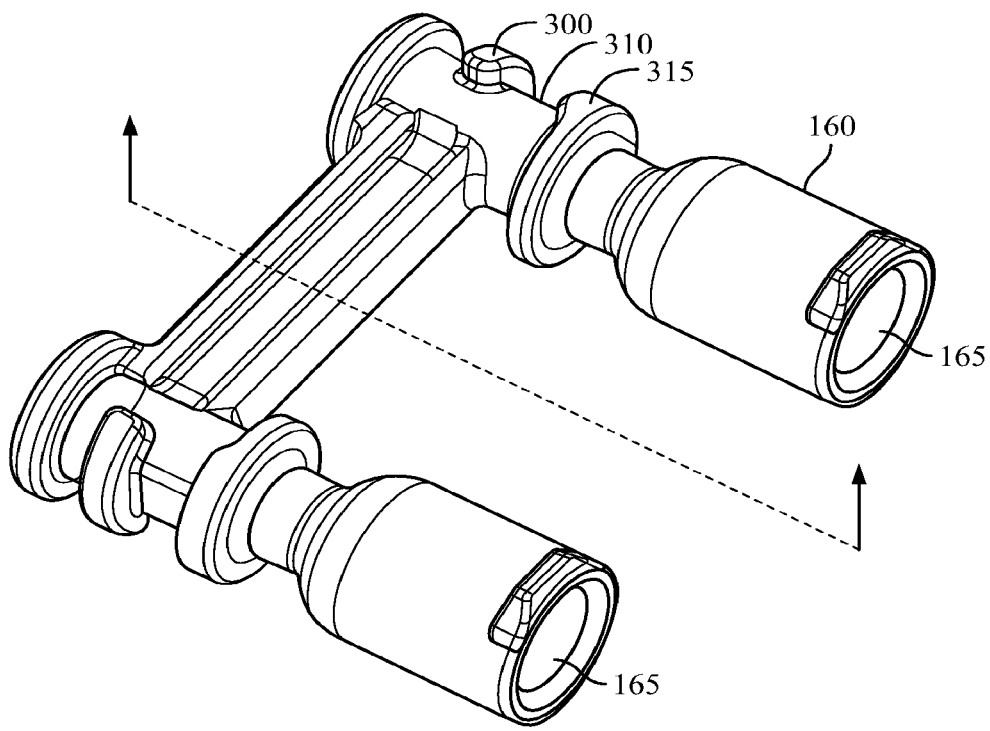
FIGS. 3A to 3D are views of the manifold of the delivery device.
Figure 3B:
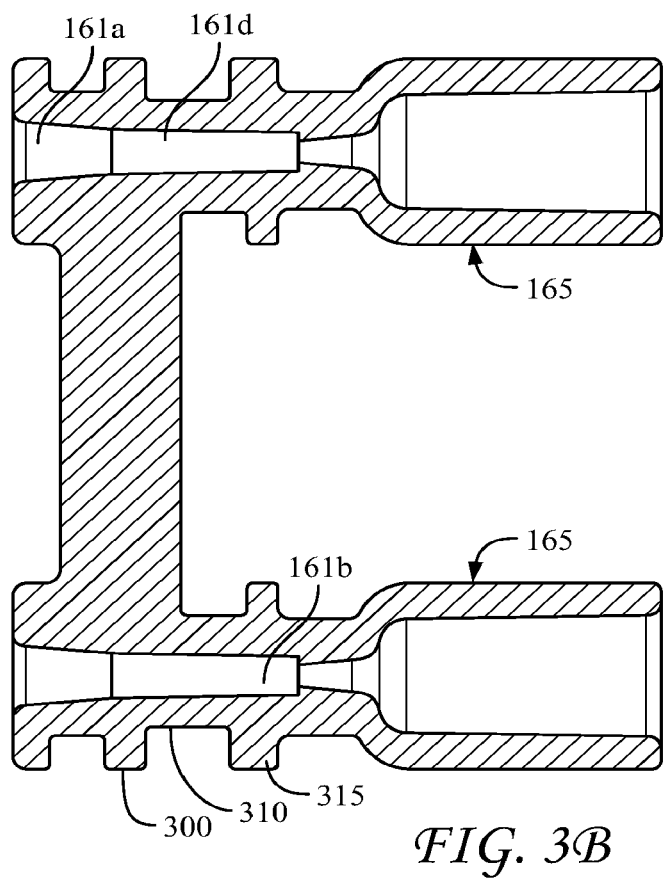
Figure 3C:
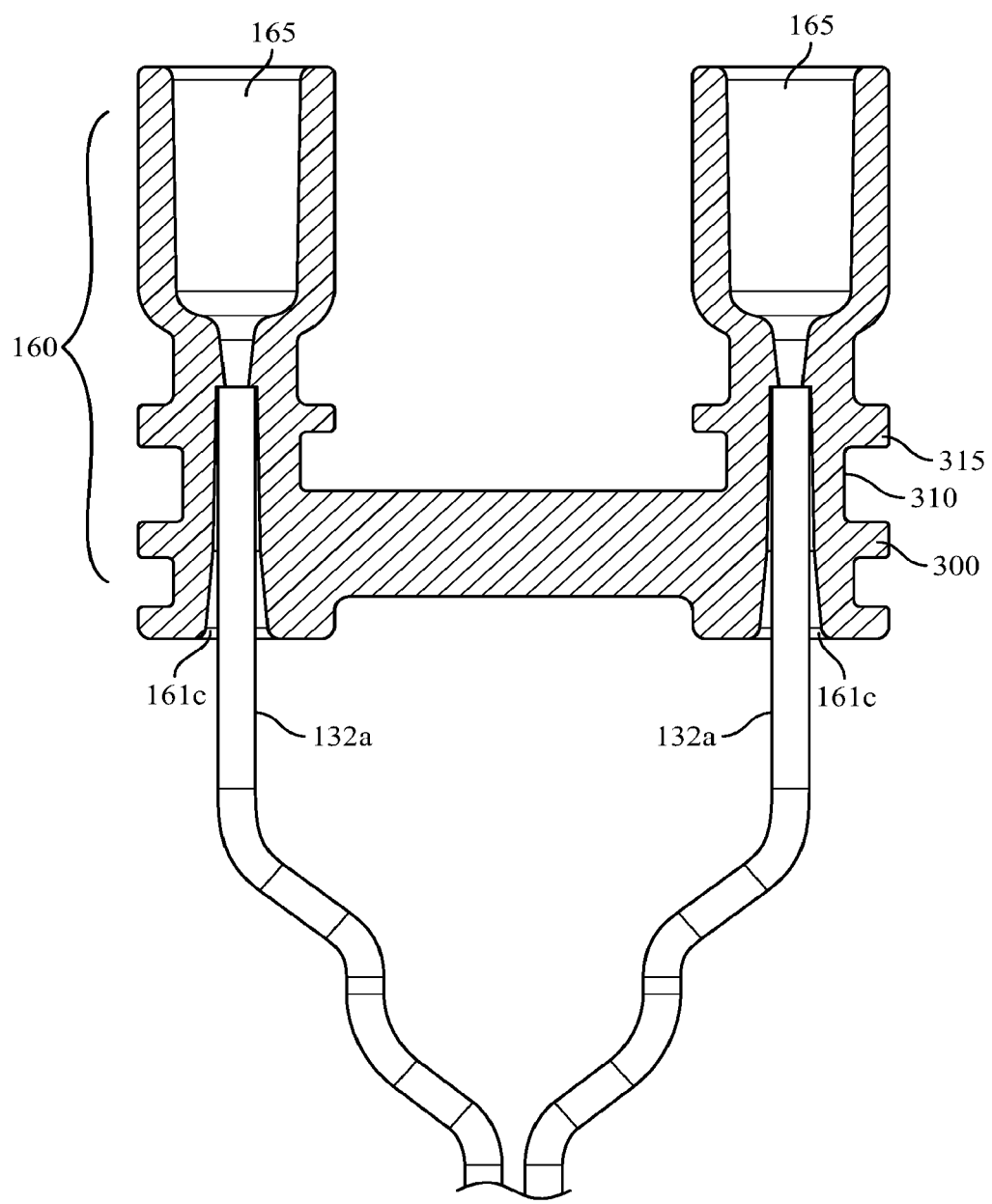

FIGS. 3A through 3C illustrate the manifold 160, which in this case is an H-connector, having two Luer-like connectors 165 on the proximal end for connection to multiple syringes containing the multiple component material. As can be seen in cross-sectional view FIG. 3B, the manifold 160 is provided with two separate lumens 161a and 161b, which extend from the distal ends of the Luer-like connectors 165 through the manifold 160, thus providing two separate fluid paths through the manifold. The distal ends of the two separate lumens 161a and 161b are structured and arranged to have first and second regions, the first regions 161c being distal to the second regions 161d and having greater diameters to accommodate the split proximal ends 132a of the side-by-side cannulae of the paratube (FIG. 3C) and simplify assembly of the dispensing device 100. Conveniently, the first regions 161c have greater tapers than the second regions 161d.

Again, it is advantageous if an adhesive is deposited in at least second regions 161d before or after insertion of the split paratube ends 132a to secure them into place within the manifold 160. Alternatively, the paratube ends can be overmolded within the manifold ends 161d.

Accordingly, it is clear that the manifold 160 and the tip connector 120 are in fluid communication by virtue of the side-by-side cannulae 132 attached to each, and in combination provide two separate fluid paths through the delivery device 100.

Figure 3D:
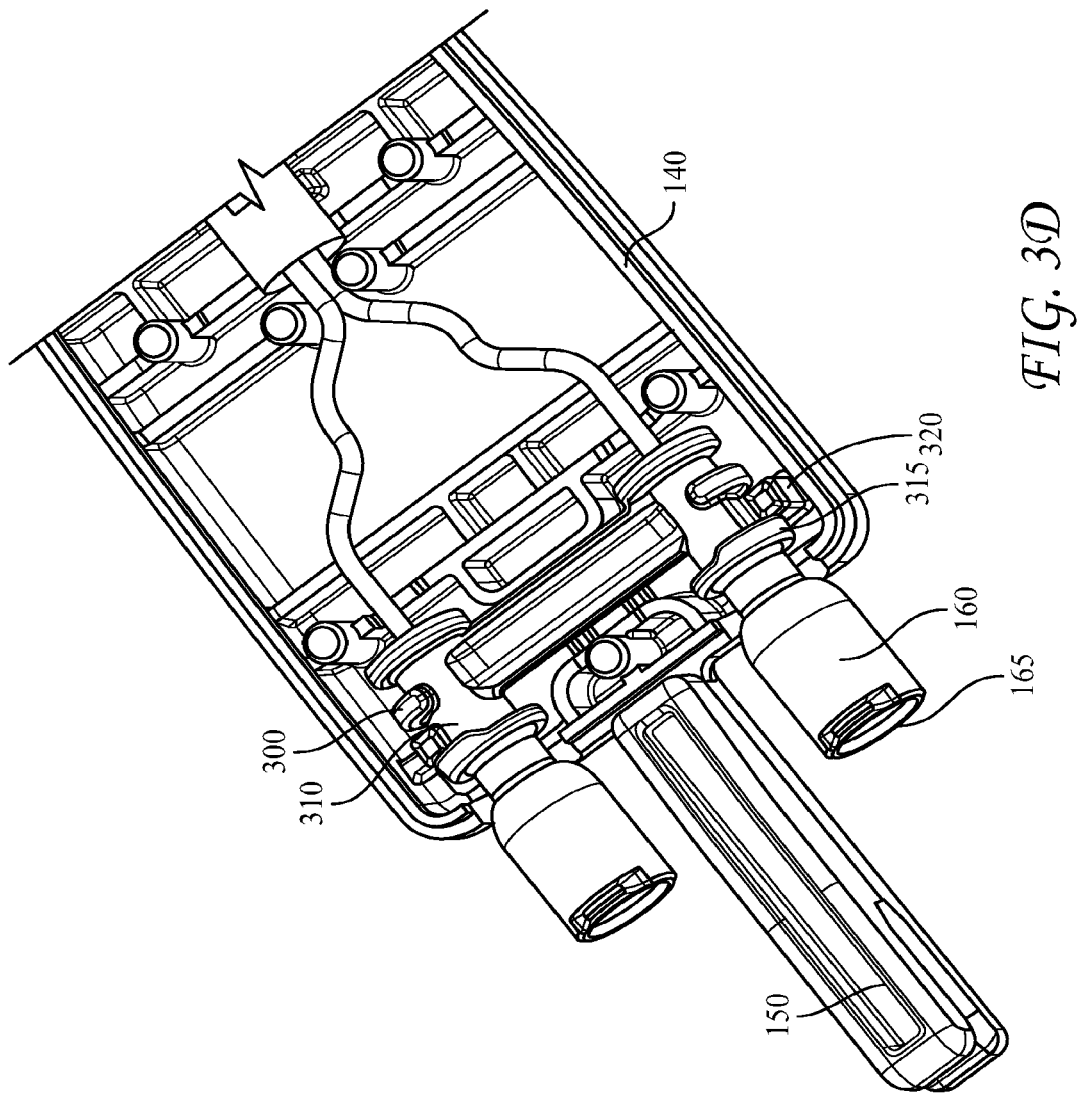

FIG. 3D shows the location of the H-connector within housing 140. The exterior of the H-connector is provided with two ridges 300, one on either side, which is a raised narrow rim which only partially surrounds the distal portions of the connector, such as being semi-circular. Likewise, the exterior of the H-connector is provided with two flanges 315 proximal to the ridges 300 which completely surround this portion of the connector. Ridges 300 and flanges 315 are separated by grooves 310, which fit against pins 320 molded into housing 140. The widths of the grooves is larger than the widths of the pins, such that the H-connector is provided with a relatively loose and slidable fit, such that the ridges 300 and pins 320 constrain the H-connector from sliding too far proximally, and the flanges 315 and pins 320 constrain the H-connector from sliding too far distally within housing 140. When either both of the ridges 300 or both of the flanges 315 are constrained against pins 320, the H-connector is centrally aligned within the housing. This slidable configuration of the H-connector is advantageous, as it provides flexibility to the fixation of the H-connector within the housing 140, as well as providing the Luer-like connectors 165 with some flexibility and limited movement outside of the housing 140, which enables easier attachment of the dual syringes 200 (FIG. 8) to the Luer-like connectors. In some embodiments there can be angular movement of the Luer-like connectors 165 relative to the centrally aligned position within the housing 140 of about 3-15 degrees, proximally and distally, such as 5 degrees, 8 degrees, 10 degrees, 12 degrees or even 15 degrees, so that the total angular movement or amplitude can be from about 6 to about 30 degrees.

FIGS. 4A through 4D show various views of the rigid overtube 130b, which can be made of any suitable rigid material capable of sterilization, such as stainless steel or any number of rigid polymers. FIG. 4B is a cutaway of the distal end of rigid overtube 130b, which shows a slot 134 which coordinates with keying feature 127 of tip connector 120 to help align the tip connector 120 with the rigid overtube 130b and prevent rotation of the connector within the overtube. Additionally, as shown in FIGS. 4C and 4D, the distal end of the rigid overtube is provided with at least one tab 136 which is biased inward, i.e. towards the interior of the tube. This tab 136 acts to capture the proximal barbed end 122 of tip connector 120 when the barbed end is inserted into the rigid overtube 130b, preventing the tip connector 120 from being inadvertently withdrawn from the overtube.

Alternatively, the overtube can be a flexible overtube 130a, as depicted in FIGS. 5A and 5B. The flexible overtube 130a can be made of any number of flexible materials, such as plastics or elastomers or the like which are capable of sterilization. The flexible overtube 130a in combination with the flexible side-by-side cannulae 132 of the paratube inside of the overtube enables the surgeon to access difficult to reach locations in vivo. The inner diameter of flexible overtube 130a is large enough to accommodate both the side-by-side cannulae 132 of the paratube and the barbed proximal end 122 of tip connector 120, which is held in place by the elasticity of the flexible overtube.

Figure 6A:
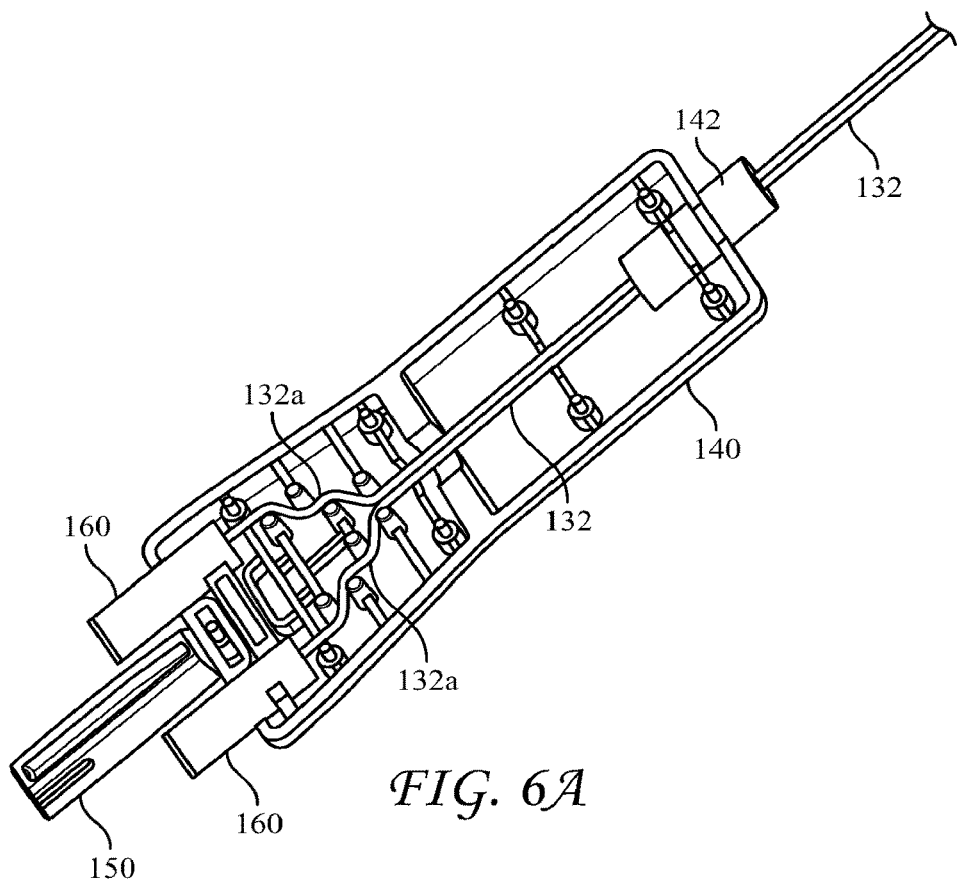
FIGS. 6A and 6B are cutaway views of housings used for the flexible overtube and rigid overtube versions of the delivery devices, respectively.
Figure 6B:
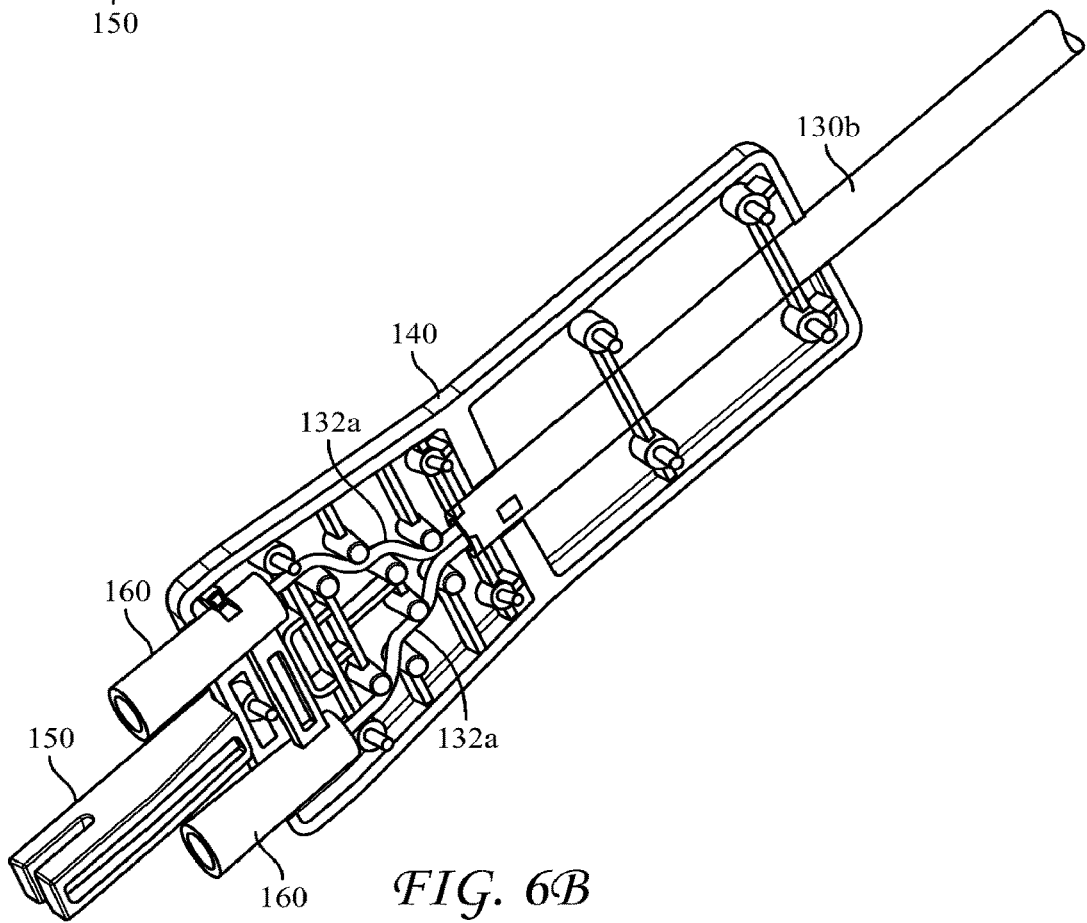

FIGS. 6A and 6B depict two versions of a lower portion of housing 140, illustrating the fluid connections between the manifold 160 and the proximal split ends 132a of the side-by-side cannulae 132 of the paratube. In FIG. 6A it can be seen that the distal end of housing 140 is provided with a grommet 142, which helps support the flexible overtube 130a, not shown in this view for clarity, and the side-by-side cannulae 132 inside of it. The proximal ends 132a of the side-by-side cannulae 132 are split and optionally routed through various pegs within the housing 140 to the separate lumens of the manifold 160. Similarly, FIG. 6B shows the location of rigid overtube 130b, which extends well into housing 140 and as such does not need a grommet for support.

Figure 7A:
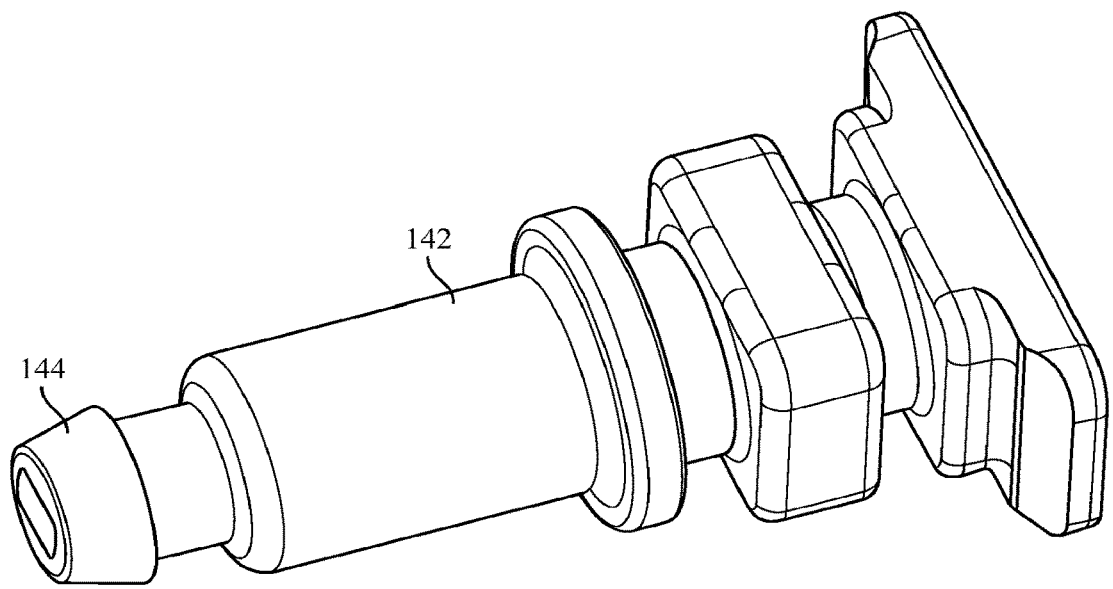
FIGS. 7A to 7E are views of a grommet useful with the flexible overtube version of the delivery device.
Figure 7B:
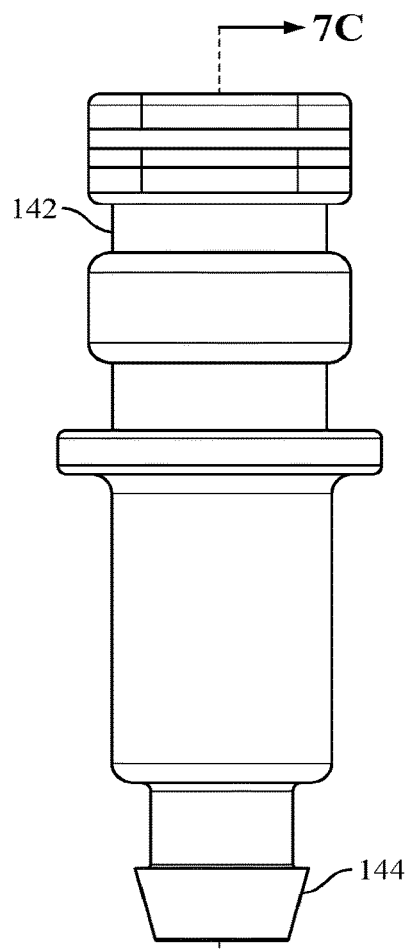
Figure 7C:
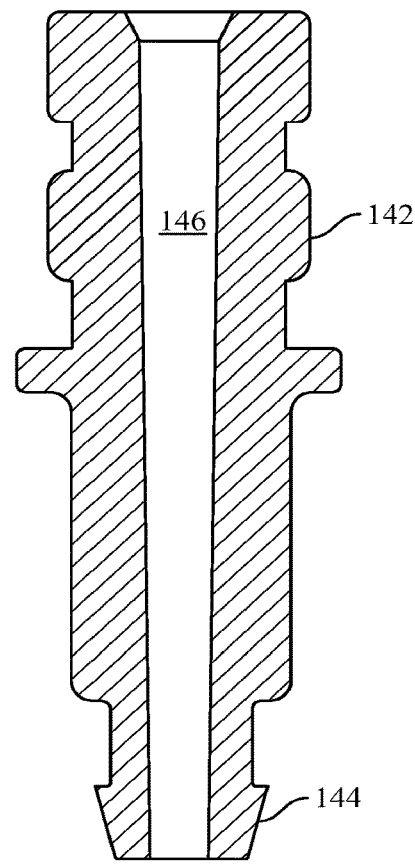
Figure 7D:
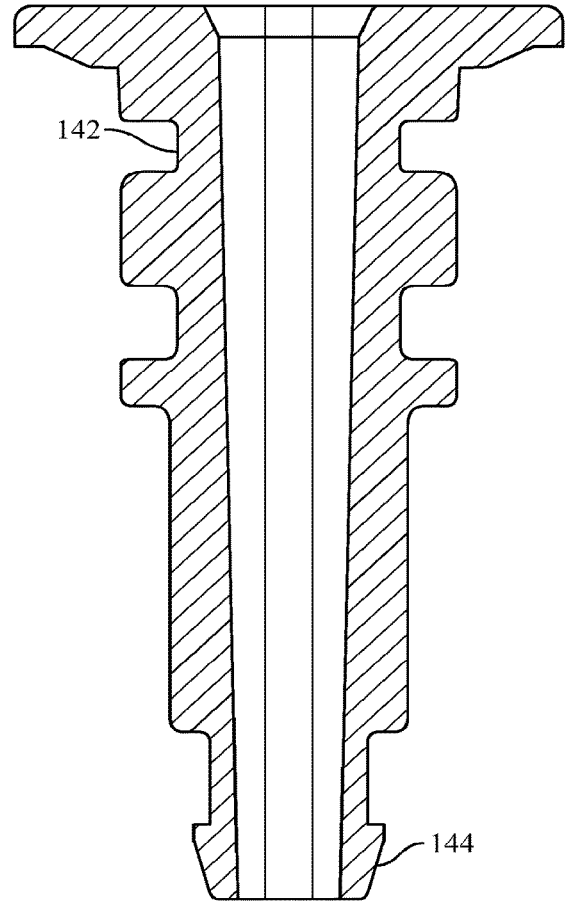
Figure 7E:
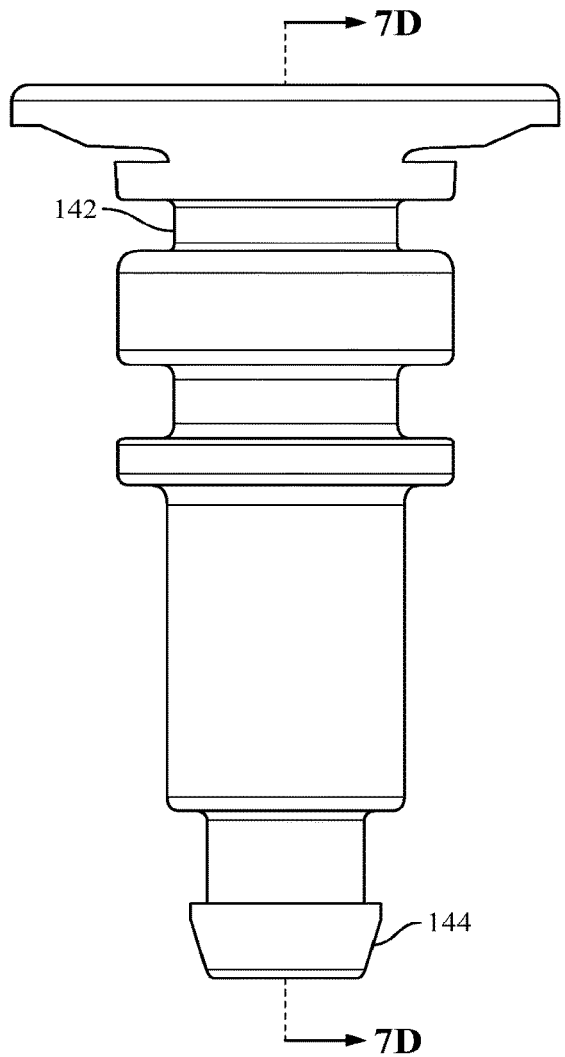

FIGS. 7A through 7C illustrate the grommet 142 used with the flexible overtube 130a version of the delivery device 100. The grommet has an internal void 146 large enough to accommodate the side-by-side cannulae or paratube 132, and a barbed distal end 144 which fits snugly into the flexible overtube 130a in much the same way as the proximal barbed end 122 of tip connector 120.

Figure 8:
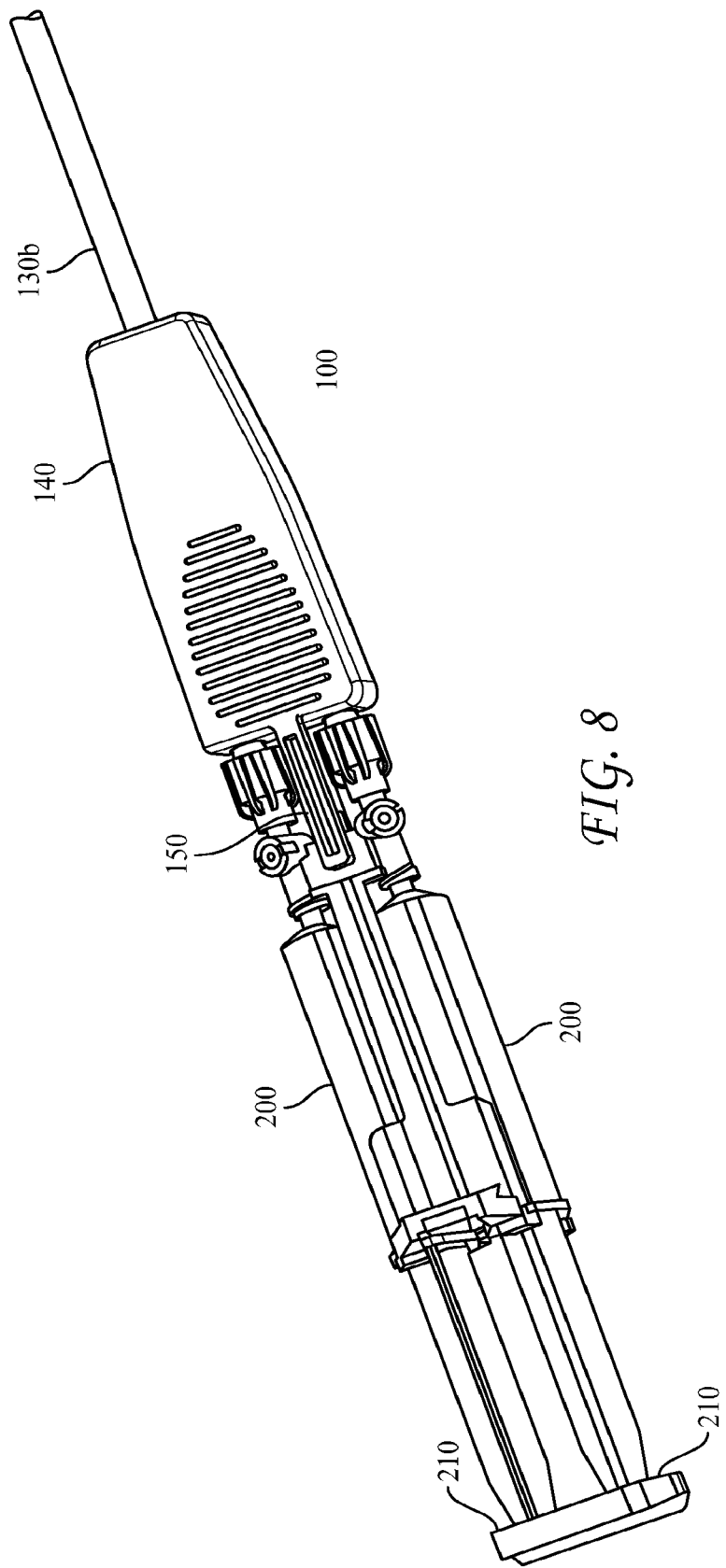
FIG. 8 is an illustration of the proximal end of the delivery device connected to a multiple syringe holder.

FIG. 8 illustrates the proximal end of the presently disclosed delivery device 100, including housing 140, rigid overtube 130b and brace 150 attached to the frame of a multiple syringe 200 having plungers 210. Upon pressing the plungers 210 which are ganged together, the separate components of the multiple component material in each syringe are delivered to the manifold 160, through the side-by-side cannulae 132 or paratube, down to the tip connector 120, through the dispensing tip and ultimately to the in vivo location to be treated.

Additionally presented is a method for delivering a multiple component material to a location in vivo, comprising supplying separate components of said multiple component material in separate syringes, compressing plungers of said separate syringes to deliver said multiple components to a manifold within a housing, the manifold having proximal and distal ends and multiple separate lumens within it, connected on its proximal end to said syringes and on its distal end to multiple flexible side-by-side cannulae, each having a proximal end and a distal end, the proximal ends of the cannulae each connected to a separate lumen at the distal end of said manifold, the distal ends of the cannulae connected to a tip connector having separate side-by-side lumens within the connector, each lumen connected to one of the flexible side-by-side cannulae, wherein said side-by-side cannulae are optionally partially connected along their length and are split at their proximal and distal ends, and passing the multiple components into a dispensing tip connected to the tip connector and then to the in vivo location.

PCT1. A dispensing device to deliver a multiple component material to a location in vivo, the device comprising a manifold having proximal and distal ends and multiple separate lumens within it, connectable on its proximal end to multiple syringes for containing the multiple component material, a distal tip assembly comprising a tip connector having separate side-by-side lumens within the tip connector and optionally a dispensing tip, and multiple flexible side-by-side cannulae, each having a proximal end and a distal end, the proximal ends of the cannulae each connected to a separate lumen at the distal end of the manifold, and the distal ends of the cannulae each connected to one of the side-by-side lumens of the tip connector, establishing a fluid communication between the manifold and the distal tip assembly, wherein said side-by-side cannulae are optionally partially connected along their length and are split at their proximal and distal ends.

PCT2. The dispensing device according to paragraph PCT1, wherein the tip connector is provided with an external thread for connecting a threaded dispensing tip and a barbed proximal end.

PCT3. The dispensing device according to paragraphs PCT1 or PCT2, wherein the distal ends of the cannulae are retained within the side-by-side lumens of the tip connector with an adhesive or by overmolding the cannulae in the lumens.

PCT4. The dispensing device according to any of paragraphs PCT1 to PCT3, further comprising a housing enclosing at least a portion of the cannulae and the manifold.

PCT5. The dispensing device according to any of paragraphs PCT1 to PCT4, wherein the tip connector comprises a distal end having two apertures, each in fluid connection with one of the side-by-side lumens therein, and can further include at least one flat surface on an outer surface thereof, or even multiple flat surfaces on an outer surface thereof.

PCT6. The dispensing device according to any of paragraphs PCT1 to PCT5, further comprising a rigid overtube through which the side-by-side cannulae extend, the rigid overtube extending between the distal tip assembly and the housing enclosing at least a portion of the manifold.

PCT7. The dispensing device according to any of paragraphs PCT1 to PCT6, wherein a barbed proximal end of the tip connector is disposed in a distal end of the rigid overtube, and the rigid overtube comprises at least one tab biased inward to retain the tip connector.

PCT8. The dispensing device according to paragraph PCT7, wherein the barbed proximal end of the tip connector is disposed in a distal end of the rigid overtube, and the rigid overtube comprises at least one slot in the distal end of the rigid overtube to align with a keying feature of the tip connector to resist rotation of the tip connector in the rigid overtube.

PCT9. The dispensing device according to any of paragraphs PCT1 to PCT5, further comprising a flexible overtube and a grommet through which the side-by-side cannulae extend, the grommet being disposed in a distal end of a housing enclosing at least a portion of the manifold, and the flexible overtube extending between the tip connector and the grommet.

PCT10. The dispensing device according to paragraph PCT9, wherein the grommet comprises a barbed distal end over which the flexible overtube is disposed and the tip connector comprises a barbed proximal end over which the flexible overtube is disposed.

PCT11. The dispensing device according to any of paragraphs PCT1 to PCT10, wherein the flexible side-by-side cannulae are partially connected along their length.

PCT12. The dispensing device according to any of paragraphs PCT1 to PCT11, wherein the manifold of the dispensing device is an H-connector having two separate lumens extending therethrough, such as wherein the distal ends of the two separate lumens in the H-connector each comprise a first region and a second region, the first region being distal with respect to the second region, the first region having a diameter greater than the second region, and the first region has a greater taper than the second region.

PCT13. The dispensing device according to paragraph PCT11, wherein the proximal ends of the cannulae are retained within the second regions of the two separate lumens with an adhesive or by overmolding the cannulae in the lumens.

PCT14. The dispensing device according to any of paragraphs PCT1 to PCT13, wherein the proximal ends of the manifold comprise Luer-taper connections for the syringes, and optionally the manifold is slidably disposed within the housing and the Luer-taper connections provide for an angular displacement relative to a centrally aligned position PCT15. The dispensing device according to any of paragraphs PCT3 to PCT14, further comprising a brace disposed at a proximal end of the housing to secure the manifold therein, extending proximally from the housing to engage with a frame for the syringes, to align the syringes with the manifold.

PCT16. A method for delivering a multiple component material to a location in vivo, comprising supplying separate components of said multiple component material in separate syringes, compressing plungers of said separate syringes to deliver said multiple components to a manifold within a housing, the manifold having proximal and distal ends and multiple separate lumens within it, connected on its proximal end to said syringes and on its distal end to multiple flexible side-by-side cannulae, each having a proximal end and a distal end, the proximal ends of the cannulae each connected to a separate lumen at the distal end of said manifold, the distal ends of the cannulae connected to a distal tip assembly comprising a tip connector having separate side-by-side lumens within the tip connector and optionally a dispensing tip, each lumen connected to one of the flexible side-by-side cannulae, wherein said side-by-side cannulae are optionally partially connected along their length and are split at their proximal and distal ends, and passing the multiple components into the tip connector, optionally through the dispensing tip and then to the in vivo location.

PCT17. The method of paragraph PCT16, wherein the multiple flexible side-by-side cannulae have a rigid overtube extending between the manifold housing and the tip connector.

PCT18. The method of paragraph PCT16, wherein the multiple flexible side-by-side cannulae have a flexible overtube extending between the manifold housing and the tip connector.

PCT19. The method of paragraphs PCT16 to PCT18, wherein the separate components do not contact one another until entering or exiting the dispensing tip.

INDUSTRIAL APPLICABILITY

The systems and methods disclosed herein are applicable to the medical device industry.

It is believed that the disclosure set forth above encompasses multiple distinct inventions with independent utility. While each of these inventions has been disclosed in its preferred form, the specific embodiments thereof as disclosed and illustrated herein are not to be considered in a limiting sense as numerous variations are possible. The subject matter of the inventions includes all novel and non-obvious combinations and subcombinations of the various elements, features, functions and/or properties disclosed herein. Similarly, where the claims recite "a" or "a first" element or the equivalent thereof, such claims should be understood to include incorporation of one or more such elements, neither requiring nor excluding two or more such elements.

It is believed that the following claims particularly point out certain combinations and subcombinations that are directed to one of the disclosed inventions and are novel and non-obvious. Inventions embodied in other combinations and subcombinations of features, functions, elements and/or properties may be claimed through amendment of the present claims or presentation of new claims in this or a related application. Such amended or new claims, whether they are directed to a different invention or directed to the same invention, whether different, broader, narrower, or equal in scope to the original claims, are also regarded as included within the subject matter of the inventions of the present disclosure.

We claim:

1. A dispensing device to deliver a multiple component material to a location in vivo, the device comprising:
   a manifold having a proximal end and a distal end and multiple separate lumens within said manifold, connectable on the proximal end of the manifold to multiple syringes for containing the multiple component material;
   a distal tip assembly comprising a tip connector having separate side-by-side lumens within the tip connector and an external thread at a distal end of the tip connector for connecting a threaded dispensing tip;
   multiple flexible side-by-side cannulae, each cannula of the cannulae having a proximal end and a distal end, the proximal end of each cannula of the cannulae each connected to a separate lumen of the multiple separate lumens at the distal end of said manifold, and the distal end of each cannula of the cannulae each connected to one of the side-by-side lumens of said tip connector, establishing a fluid communication between said manifold and said distal tip assembly, wherein said side-by-side cannulae are optionally partially connected along a length and are split at the proximal end of each cannula of the cannulae and the distal end of each cannula of the cannulae; and
   a rigid tube through which the side-by-side cannulae extend, the rigid tube extending between the distal tip assembly and a housing enclosing at least a portion of the manifold;
   wherein the distal end of each cannula of the cannulae is retained within the side-by-side lumens of the tip connector with an adhesive or by overmolding the cannulae in the side-by-side lumens.

2. The dispensing device of claim 1, wherein said tip connector is provided with a barbed proximal end.

3. The dispensing device of claim 1, wherein the housing encloses at least a portion of the cannulae.

4. The dispensing device of claim 3, wherein the proximal end of the manifold comprises Luer-taper connections for the syringes, the manifold is slidably disposed within the housing and the Luer-taper connections provide for an angular displacement relative to a centrally aligned position.

5. The dispensing device of claim 1, wherein the distal end of the tip connector comprises two apertures within the tip connector.

6. The dispensing device of claim 1, wherein the tip connector comprises at least one flat surface on an outer surface thereof.

7. The dispensing device of claim 1, wherein the tip connector comprises multiple flat surfaces on an outer surface thereof.

8. The dispensing device of claim 7, wherein a barbed proximal end of the tip connector is disposed in a distal end of the rigid tube, and the rigid tube comprises at least one tab biased inward to retain the tip connector.

9. The dispensing device of claim 8, wherein the rigid tube comprises at least one slot in the distal end of the rigid tube to align with a keying feature of the tip connector to resist rotation of the tip connector in the rigid tube.

10. The dispensing device of claim 1, wherein the flexible side-by-side cannulae are partially connected along their length.

11. The dispensing device of claim 1, wherein the manifold is an H-connector having two separate lumens extending therethrough.

12. The dispensing device of claim 11, wherein a distal end of each of the two separate lumens in the H-connector each comprise a first region and a second region, the first region being distal with respect to the second region, the first region having a diameter greater than a diameter of the second region.

13. The dispensing device of claim 12, wherein the first region has a greater taper than the second region.

14. The dispensing device of claim 12, wherein the proximal end of each cannula of the cannulae is retained within the second region of each of the two separate lumens with an adhesive or by overmolding the cannulae in the two separate lumens.

15. The dispensing device of claim 1, wherein the proximal end of the manifold comprises Luer-taper connections for the syringes.

16. A dispensing device to deliver a multiple component material to a location in vivo, the device comprising:
   a manifold having a proximal end and a distal end and multiple separate lumens within said manifold, connectable on the proximal end of the manifold to multiple syringes for containing the multiple component material;
   a distal tip assembly comprising a tip connector having separate side-by-side lumens within the tip connector and an external thread at a distal end of the tip connector for connecting a threaded dispensing tip;
   multiple flexible side-by-side cannulae, each cannula of the cannulae having a proximal end and a distal end, the proximal end of each cannula of the cannulae connected to a separate lumen of the multiple separate lumens at the distal end of said manifold, and the distal end of each cannula of the cannulae each connected to one of the side-by-side lumens of said tip connector, establishing a fluid communication between said manifold and said distal tip assembly, wherein said side-by-side cannulae are optionally partially connected along a length and are split at the proximal end of each cannula of the cannulae and the distal end of each cannula of the cannulae;
a housing enclosing at least a portion of the cannulae and the manifold;
wherein the proximal end of the manifold comprises Luer-taper connections for the syringes, the manifold is slidably disposed within the housing and the Luer-taper connections provide for an angular displacement relative to a centrally aligned position; and
wherein the distal end of each cannula of the cannulae is retained within the side-by-side lumens of the tip connector with an adhesive or by overmolding the cannulae in the side-by-side lumens.

17. The dispensing device of claim 16, wherein said tip connector is provided with a barbed proximal end.

18. The dispensing device of claim 16, wherein the distal end of the tip connector comprises two apertures, each in fluid connection with one of the side-by-side lumens within the tip connector.

19. The dispensing device of claim 16, wherein the tip connector comprises at least one flat surface on an outer surface thereof.

20. The dispensing device of claim 16, wherein the tip connector comprises multiple flat surfaces on an outer surface thereof.

21. The dispensing device of claim 16, further comprising a rigid tube through which the side-by-side cannulae extend, the rigid tube extending between the distal tip assembly and the housing.

22. The dispensing device of claim 21, wherein a barbed proximal end of the tip connector is disposed in a distal end of the rigid tube, and the rigid tube comprises at least one tab biased inward to retain the tip connector.

23. The dispensing device of claim 22, wherein the rigid tube comprises at least one slot in the distal end of the rigid tube to align with a keying feature of the tip connector to resist rotation of the tip connector in the rigid tube.

24. The dispensing device of claim 16, wherein the flexible side-by-side cannulae are partially connected along their length.

25. The dispensing device of claim 16, wherein the manifold is an H-connector having two separate lumens extending therethrough.

26. The dispensing device of claim 25, wherein a distal end of each of the two separate lumens in the H-connector each comprise a first region and a second region, the first region being distal with respect to the second region, the first region having a diameter greater than a diameter of the second region.

27. The dispensing device of claim 26, wherein the first region has a greater taper than the second region.

28. The dispensing device of claim 26, wherein the proximal end of each cannula of the cannulae is retained within the second region of each of the two separate lumens with an adhesive or by overmolding the cannulae in the two separate lumens.

29. The dispensing device of claim 16, further comprising a brace disposed at a proximal end of the housing to secure the manifold within the housing, extending proximally from the housing to engage with a frame for the syringes, to align the syringes with the manifold.

30. A dispensing device to deliver a multiple component material to a location in vivo, the device comprising:
a manifold having a proximal end and a distal end and multiple separate lumens within said manifold, connectable on the proximal end of the manifold to multiple syringes for containing the multiple component material;
a distal tip assembly comprising a tip connector having separate side-by-side lumens within the tip connector and an external thread at a distal end of the tip connector for connecting a threaded dispensing tip;
multiple flexible side-by-side cannulae, each cannula of the cannulae having a proximal end and a distal end, the proximal end of each cannula of the cannulae each connected to a separate lumen of the multiple separate lumens at the distal end of said manifold, and the distal end of each cannula of the cannulae each connected to one of the side-by-side lumens of said tip connector, establishing a fluid communication between said manifold and said distal tip assembly, wherein said side-by-side cannulae are optionally partially connected along a length and are split at the proximal end of each cannula of the cannulae and the distal end of each cannula of the cannulae;
a housing enclosing at least a portion of the cannulae and the manifold; and
a brace disposed at a proximal end of the housing to secure the manifold within the housing, extending proximally from the housing to engage with a frame for the syringes, to align the syringes with the manifold.

31. The dispensing device of claim 30, wherein said tip connector is provided with a barbed proximal end.

32. The dispensing device of claim 30, wherein the distal end of each cannula of the cannulae is retained within the side-by-side lumens of the tip connector with an adhesive or by overmolding the cannulae in the side-by-side lumens.

33. The dispensing device of claim 30, wherein the distal end of the tip connector comprises two apertures, each in fluid connection with one of the side-by-side lumens within the tip connector.

34. The dispensing device of claim 30, wherein the tip connector comprises at least one flat surface on an outer surface thereof.

35. The dispensing device of claim 30, wherein the tip connector comprises multiple flat surfaces on an outer surface thereof.

36. The dispensing device of claim 30, further comprising a rigid tube through which the side-by-side cannulae extend, the rigid tube extending between the distal tip assembly and the housing.

37. The dispensing device of claim 36, wherein a barbed proximal end of the tip connector is disposed in a distal end of the rigid tube, and the rigid tube comprises at least one tab biased inward to retain the tip connector.

38. The dispensing device of claim 37, wherein the rigid tube comprises at least one slot in the distal end of the rigid tube to align with a keying feature of the tip connector to resist rotation of the tip connector in the rigid tube.

39. The dispensing device of claim 30, wherein the flexible side-by-side cannulae are partially connected along their length.

40. The dispensing device of claim 30, wherein the manifold is an H-connector having two separate lumens extending therethrough.

41. The dispensing device of claim 40, wherein a distal end of each of the two separate lumens in the H-connector each comprise a first region and a second region, the first region being distal with respect to the second region, the first region having a diameter greater than a diameter of the second region.

42. The dispensing device of claim 41, wherein the first region has a greater taper than the second region.

43. The dispensing device of claim 41, wherein the proximal end of each cannula of the cannulae is retained within the second region of each of the two separate lumens with an adhesive or by overmolding the cannulae in the two separate lumens.

44. The dispensing device of claim 30, wherein the proximal end of the manifold comprises Luer-taper connections for the syringes.

45. The dispensing device of claim 30, wherein the proximal of end the manifold comprises Luer-taper connections for the syringes, the manifold is slidably disposed within the housing and the Luer-taper connections provide for an angular displacement relative to a centrally aligned position.

46. A dispensing device to deliver a multiple component material to a location in vivo, the device comprising:
- a manifold having a proximal end and a distal end and multiple separate lumens within said manifold, connectable on the proximal end of the manifold to multiple syringes for containing the multiple component material;
- a distal tip assembly comprising a tip connector having separate side-by-side lumens within the tip connector and an external thread at a distal end of the tip connector for connecting a threaded dispensing tip;
- multiple flexible side-by-side cannulae, each cannula of the cannulae having a proximal end and a distal end, the proximal end of each cannula of the cannulae each connected to a separate lumen of the multiple separate lumens at the distal end of said manifold, and the distal end of each cannula of the cannulae each connected to one of the side-by-side lumens of said tip connector, establishing a fluid communication between said manifold and said distal tip assembly, wherein said side-by-side cannulae are optionally partially connected along a length and are split at the proximal end of each cannula of the cannulae and the distal end of each cannula of the cannulae;
- a rigid tube through which the side-by-side cannulae extend, the rigid tube extending between the distal tip assembly and a housing;
- wherein the housing encloses at least a portion of the cannulae;
- a brace disposed at a proximal end of the housing to secure the manifold within the housing, extending proximally from the housing to engage with a frame for the syringes, to align the syringes with the manifold; and
- wherein the distal end of each cannula of the cannulae is retained within the side-by-side lumens of the tip connector with an adhesive or by overmolding the cannulae in the side-by-side lumens.

47. A dispensing device to deliver a multiple component material to a location in vivo, the device comprising:
- a manifold having a proximal end and a distal end and multiple separate lumens within said manifold, connectable on the proximal end of the manifold to multiple syringes for containing the multiple component material;
- a distal tip assembly comprising a tip connector having separate side-by-side lumens within the tip connector and an external thread at a distal end of the tip connector for connecting a threaded dispensing tip;
- multiple flexible side-by-side cannulae, each cannula of the cannulae having a proximal end and a distal end, the proximal end of each cannula of the cannulae each connected to a separate lumen of the multiple separate lumens at the distal end of said manifold, and the distal end of each cannula of the cannulae each connected to one of the side-by-side lumens of said tip connector, establishing a fluid communication between said manifold and said distal tip assembly, wherein said side-by-side cannulae are optionally partially connected along a length and are split at the proximal end of each cannula of the cannulae and the distal end of each cannula of the cannulae;
- a housing enclosing at least a portion of the cannulae and the manifold;
- a brace disposed at a proximal end of the housing to secure the manifold within the housing, extending proximally from the housing to engage with a frame for the syringes, to align the syringes with the manifold; and
- wherein the proximal end of the manifold comprises Luer-taper connections for the syringes, the manifold is slidably disposed within the housing and the Luer-taper connections provide for an angular displacement relative to a centrally aligned position.

* * * * *